United States Patent [19]
Hurley et al.

[11] Patent Number: 5,331,846
[45] Date of Patent: Jul. 26, 1994

[54] LONG DURATION ASH PROBE

[75] Inventors: John P. Hurley; Don P. McCollor, both of Grand Forks, N. Dak.; Stanley J. Selle, Grand Forks, Minn.

[73] Assignee: Energy & Environmental Research Center Foundation, Grand Forks, N. Dak.

[21] Appl. No.: 885,655

[22] Filed: May 19, 1992

[51] Int. Cl.⁵ ............................................. G01N 17/00
[52] U.S. Cl. ................................................... 73/86
[58] Field of Search ............... 73/86, 866.5, 865.8, 73/863.82, 623, 23.31-23.33, 28.01

[56] References Cited

U.S. PATENT DOCUMENTS

| | | | |
|---|---|---|---|
| 1,683,489 | 9/1928 | Rice | 73/86 |
| 2,864,252 | 12/1956 | Schaschl | 73/86 |
| 3,174,332 | 4/1961 | Echtler, Jr. et al. | 73/86 |
| 3,627,493 | 12/1971 | Manley | 73/86 |
| 3,718,034 | 2/1973 | Swearingen | 73/86 |
| 3,861,876 | 1/1975 | Robertson et al. | 73/86 |
| 4,002,059 | 1/1977 | Jeffers et al. | 73/86 |
| 4,095,474 | 6/1978 | Hancock et al. | 73/86 |
| 4,179,920 | 12/1979 | Schuller et al. | 73/86 |
| 4,228,676 | 10/1980 | Myers | 73/28 |
| 4,387,592 | 6/1983 | Welker | 73/198 |
| 4,665,760 | 5/1987 | Eramo et al. | 73/866.5 |
| 5,131,284 | 7/1992 | Radziun et al. | 73/866.5 |

FOREIGN PATENT DOCUMENTS 482539 4/1952 Canada .............................. 73/863.82

*Primary Examiner*—Robert Raevis
*Attorney, Agent, or Firm*—Zarley, McKee, Thomte Voorhees & Sease

[57] ABSTRACT

A long duration ash probe includes a pressure shell connected to a port in a combustor with a sample coupon mounted on a retractable carriage so as to retract the sample coupon within the pressure shell during sootblowing operation of the combustor. A valve mounted at the forward end of the pressure shell is selectively closeable to seal the sample coupon within the shell, and a heating element in the shell is operable to maintain the desired temperature of the sample coupon while retracted within the shell. The carriage is operably mounted on a pair of rails within the shell for longitudinal movement within the shell. A hollow carrier tube connects the hollow cylindrical sample coupon to the carriage, and extends through the carriage and out the rearward end thereof. Air lines are connected to the rearward end of the carrier tube and are operable to permit coolant to pass through the air lines and thence through the carrier tube to the sample coupon so as to cool the sample coupon.

14 Claims, 5 Drawing Sheets

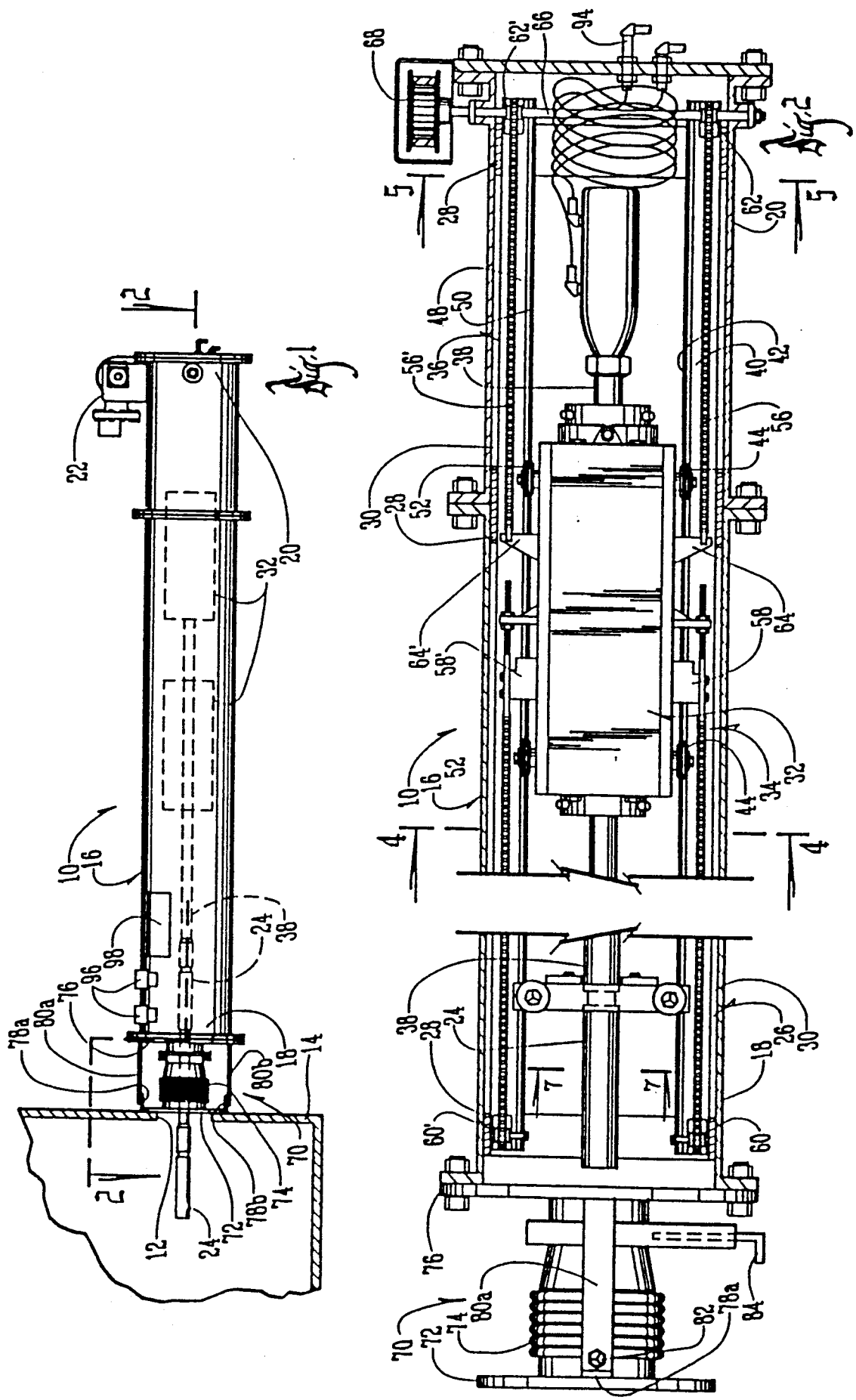

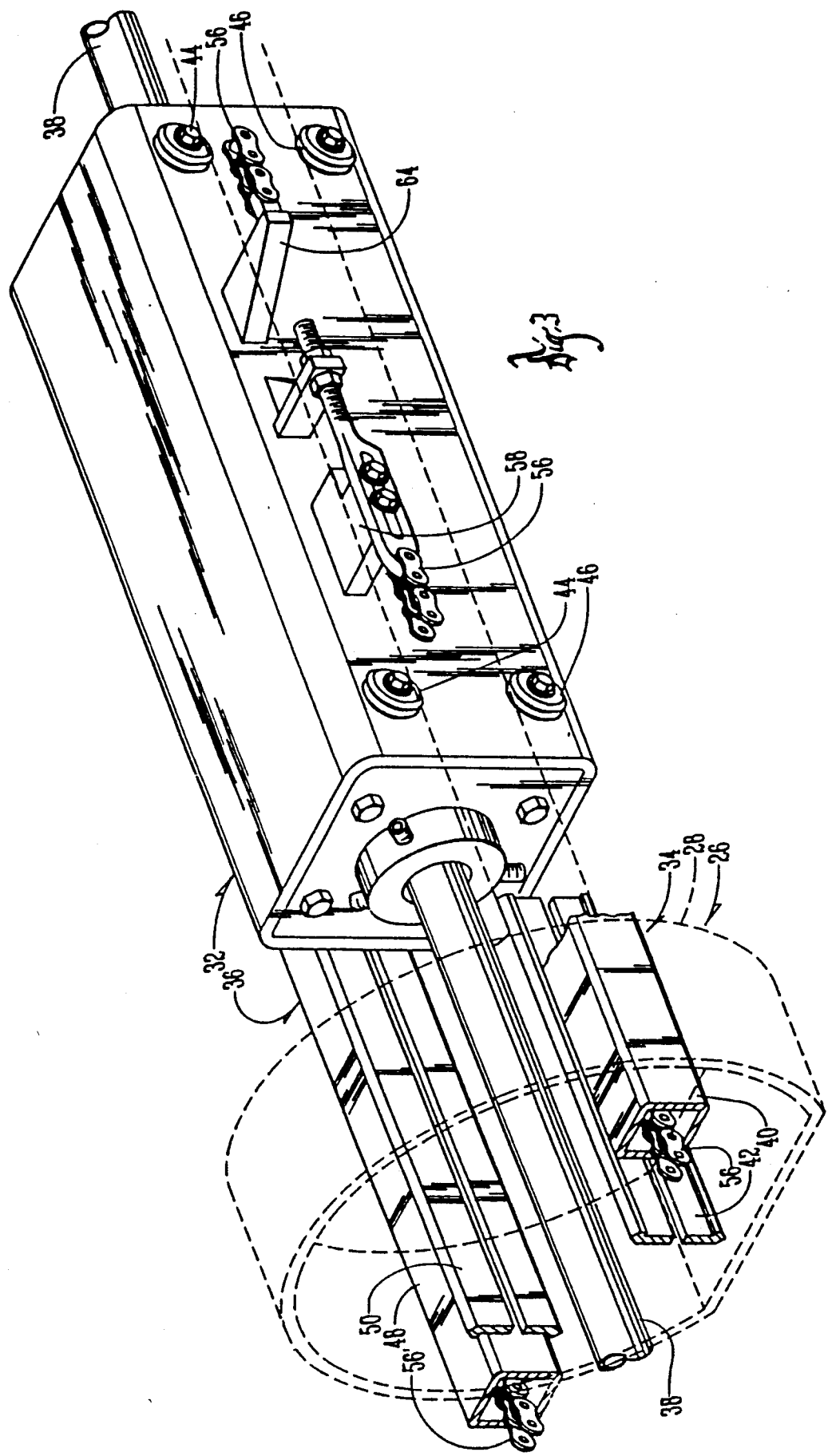

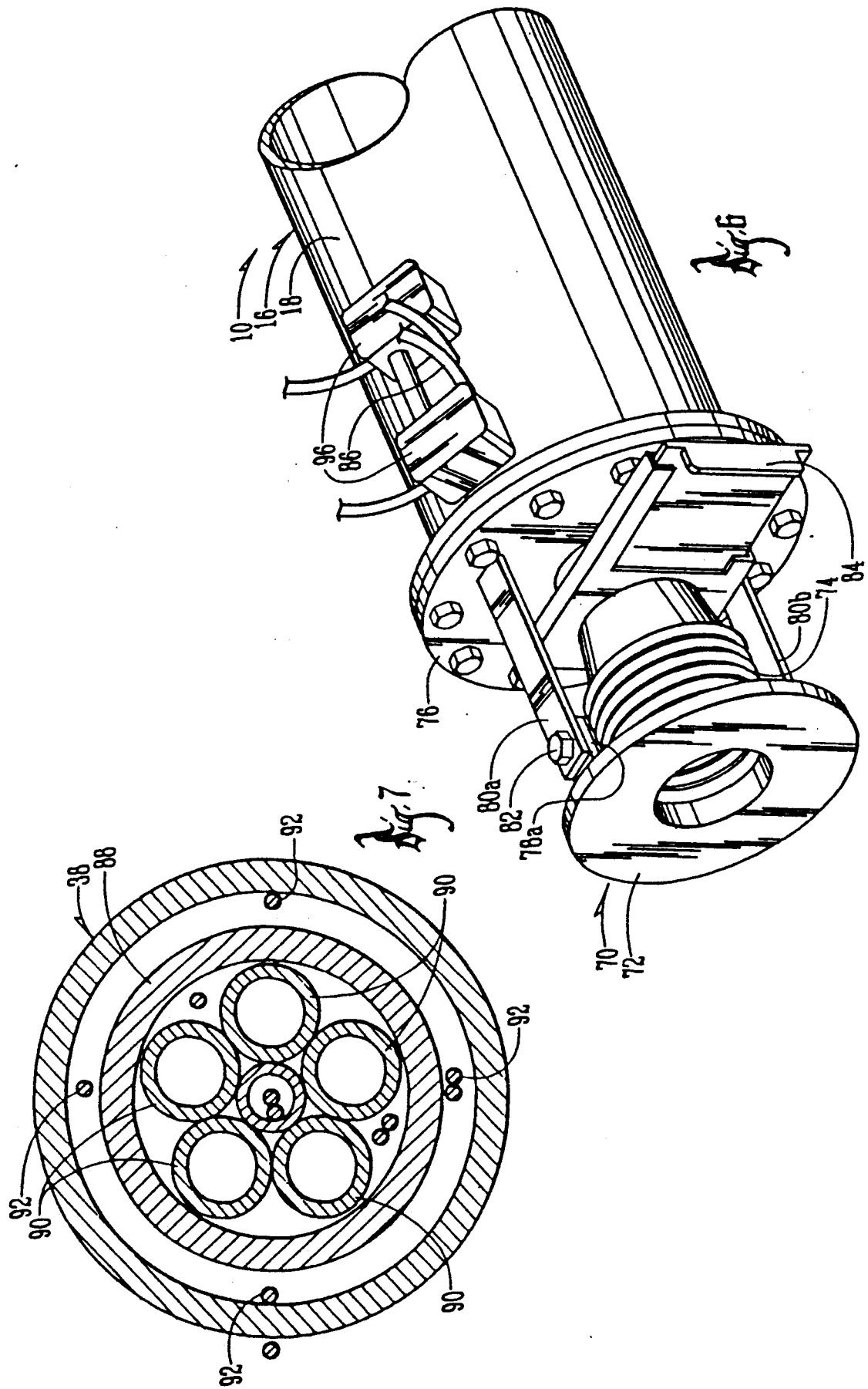

LONG DURATION ASH PROBE

STATEMENT OF GOVERNMENT INTEREST

This invention was made in part with government support under Cooperative Agreement DE-FC21-86MC10637 with the Department of Energy. The government has certain rights in this invention.

TECHNICAL FIELD

The present invention relates generally to probes for sampling ash deposits in combustion units, and more particularly to an improved probe which is automated to retract the probe during sootblowing operations, so as to permit long duration of the probe within a combustion chamber.

BACKGROUND OF THE INVENTION

In order to assess the effects of ash formation on boiler tubes, it was common to insert a small tube through a hole in the combustor wall of the boiler. The main problem with such prior art devices was in the accurate assessment of ash formation on a boiler tube under conditions similar to the actual boiler tubes in a combustion unit. Prior art devices were not capable of long duration since the sootblowing operation of conventional combustion units would disturb the ash deposit on the sample probe.

In addition, the coupon and ash temperature could not be maintained outside the combustor in prior art devices.

It is therefore a general object of the present invention to provide an improved long duration ash probe.

Another object of the present invention is to provide an ash probe which is automatically retractable from the combustion unit during sootblowing operations of the combustion unit.

Still another object is to provide a long duration ash probe capable of monitoring and controlling the temperature of the coupon thereof.

These and other objects will be apparent to those skilled in the art.

SUMMARY OF THE INVENTION

The long duration ash probe of the present invention includes a pressure shell connected to a port in a combustor with a sample coupon mounted on a retractable carriage so as to retract the sample coupon within the pressure shell during sootblowing operation of the combustor. A valve mounted at the forward end of the pressure shell is selectively closeable to seal the sample coupon within the shell, and a heating element in the shell is operable to maintain the desired temperature the sample coupon while retracted within the shell. The carriage is operably mounted on a pair of rails within the shell for longitudinal movement within the shell. A hollow carrier tube connects the hollow cylindrical sample coupon to the carriage, and extends through the carriage and out the rearward end thereof. Tubing is mounted within the carrier tube and extends from the forward end to the rearward end. Air lines are connected to the rearward end of the tubing and valves in the air lines are operable to permit coolant to pass through the air lines and thence through the tubing to the sample coupon so as to cool the sample coupon. Thermocouples mounted in the carrier tube adjacent the sample coupon since the temperature at the coupon and are interconnected to a central control so as to selectively operate the air line valves to maintain the sample coupon at the desired temperature. The central control may also be interconnected with the combustor control so as to automatically retract the sample coupon during sootblowing operations and then re-extend the coupon into the combustor, so as to enable a long duration of time within the combustor without the effects of sootblowing thereon.

BRIEF DESCRIPTION OF THE DRAWINGS

FIG. 1 is a side view of the probe of the present invention installed in a combustion unit;

FIG. 2 is an enlarged cross-sectional view taken at lines 2—2 in FIG. 1;

FIG. 3 is a super enlarged perspective view of the carriage supporting the probe of the present invention;

FIG. 6 is a perspective view of the forward end of the probe;

FIG. 7 is an enlarged cross-sectional view taken at lines 7—7 in FIG. 2; and

DESCRIPTION OF THE PREFERRED EMBODIMENT

Figure 4:
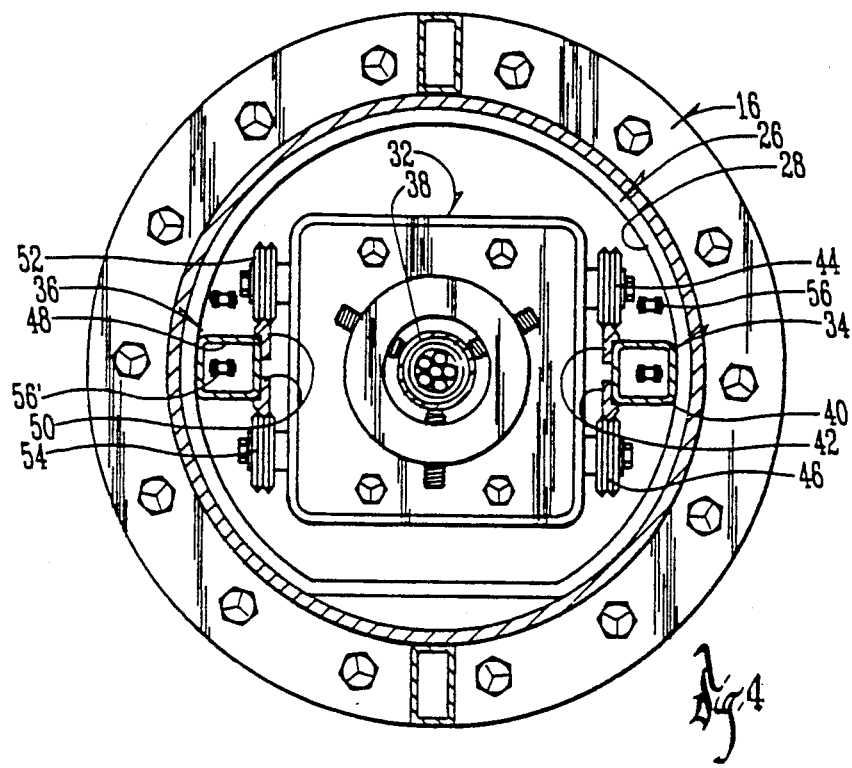
FIG. 4 is a cross-sectional view taken at lines 4—4 in FIG. 2.

Referring now to the drawings, in which similar or corresponding parts are identified with the same reference numeral, and more particularly to FIG. 1, the long duration ash probe of the present invention is designated generally at 10 and is shown mounted to a port 12 on a combustor unit 14. Probe 10 includes an elongated hollow cylindrical pressure shell 16 having a forward end 18 and rearward end 20. A motor 22 is mounted on rearward end 20 of shell 16 and serves to extend and retract a sample coupon 24 from combustor unit 14.

Referring now to FIGS. 2 and 3, shell 16 has a carriage assembly 26 removably mounted therein, including a frame work of metal rings 28 interconnected by flat straps 30 to form an elongated hollow cylindrical frame work which may be inserted within shell 16. Carriage assembly 26 includes a carriage 32 operably mounted on a pair of spaced-apart rails 34 and 36 to permit movement of carriage 32 forwardly and rearwardly within shell 16. Carriage 32 has a generally hollow rectangular housing which supports a hollow carrier tube 38 located coaxially along the longitudinal axis of carriage 32. Sample coupon 24 is threaded to the forward end of carrier tube 38, for movement with carrier tube 38 and carriage 32.

Rail 34 includes a hollow square tubular portion 40 with a generally vertically oriented track 42 mounted to one surface thereof, and extends from the forward to the rearward end of carriage assembly 26. A pair of upper rollers 44 and lower rollers 46 are mounted on the corresponding side of carriage 32 and are shaped to receive the upper and lower edges of track 42 therebetween to guide carriage 32 along rail 34. As shown in FIG. 4, rail 36 is similar to rail 34, and includes a square tubular portion 48 with a vertical track 50 attached to one face thereof, upon which upper rollers 52 and lower rollers 54 are engaged.

Figure 5:
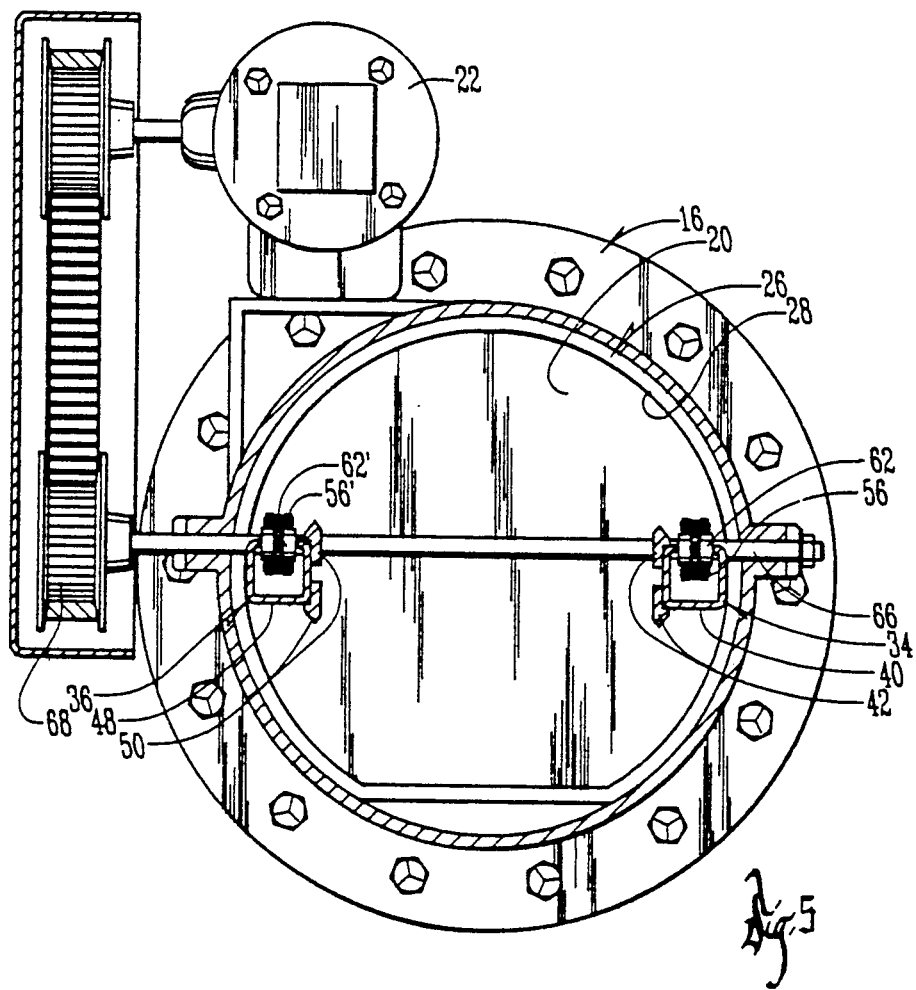
FIG. 5 is a cross-sectional view taken at lines 5—5 in FIG. 2.

A chain or cable 56 is connected in an endless loop to an arm 58 mounted on one side of carriage 32. As shown in FIG. 2, chain 56 extends from arm 58 forwardly around an idler sprocket 60 and thence rearwardly journaled through tube 40 (as shown in FIG. 4) around drive sprocket 62 (as shown in FIG. 5), and thence forwardly to a rearward arm 64 on carriage 32. In this fashion, rotation of drive sprocket 62 in one direction will move carriage 32 forwardly, while rotation of drive sprocket 62 in the opposite direction will move carriage 32 rearwardly. A similar arrangement is utilized on the opposing side of carriage 32, with chain 56' connected to an arm 58', extending forwardly around an idler sprocket 60', thence rearwardly to drive sprocket 62', and thence forwardly to a rearward arm 64'. A drive shaft 66 connects drive sprockets 62 and 62' (as shown in FIGS. 2 and 5) and extends outwardly to a drive pulley 68 which is connected to motor 22. In this way, motor 22 will extend or retract coupon sample 24 by moving carriage 32 forwardly or rearwardly in carriage assembly 26.

A connector assembly 70 interconnects the forward end 18 of pressure shell 16 to the combustor wall. Connector assembly 70 includes a forward flange 72 which is bolted directly to the combustor wall, and a thermal expansion tube 74 extending from forward flange 72 to a rearward flange 76 which connects to the forward end 18 of pressure shell 16. A pair of arms 78a and 78b project rearwardly from forward flange 72, and selectively connect to forwardly projecting arms 80a and 80b mounted on rearward flange 76, respectively. A bolt 82 interconnects arms 78a and 80a and arms 78b and 80b through a slot formed in arms 80a and 80b, to permit selective adjustment of the distance between forward flange 72 and rearward flange 76 due to thermal stress. Thermal expansion tube 74 of connector assembly 70 allows for thermal stress relief between the carriage unit and combustor wall. A valve 84 is interposed between the thermal expansion tube 74 and rearward flange 76, and is operable to seal off the entire interior of pressure shell 16 from the combustion chamber, while containing the coupon probe 24 therein. A split electric tube furnace is mounted within shell 16 proximal the forward end 18 to maintain the temperature of the sample coupon when retracted within shell 16, and has electrical connections 96 extending through the wall of shell 16 for connection to a power source. Thermocouples 86 (see FIG. 6) extend through shell 16 into the heating zone of the tube furnace to monitor and control the temperature of the tube furnace.

Referring now to FIG. 7, carrier tube 38 is enlarged in cross-section to show that it houses a smaller coaxial interior tube 88 and a plurality of small diameter tubing 90 within interior tube 88. A series of thermocouples 92 are mounted between interior tube 88 and carrier tube 38, and extend generally forwardly to the sample coupon. Thermocouples 92 measure the temperature at the sample coupon and transmit that information to a control box (not shown). A pair of airline connections 94 (shown in FIG. 2) will communicate compressed air into the rearward end of carrier tube 38 and thence through tubing 90, through sample coupon 24 and into the combustor, so as to cool the sample coupon and maintain the coupon at a set temperature. Additional sensors (as shown in FIG. 7) may be utilized to measure other pertinent information.

Figure 8:
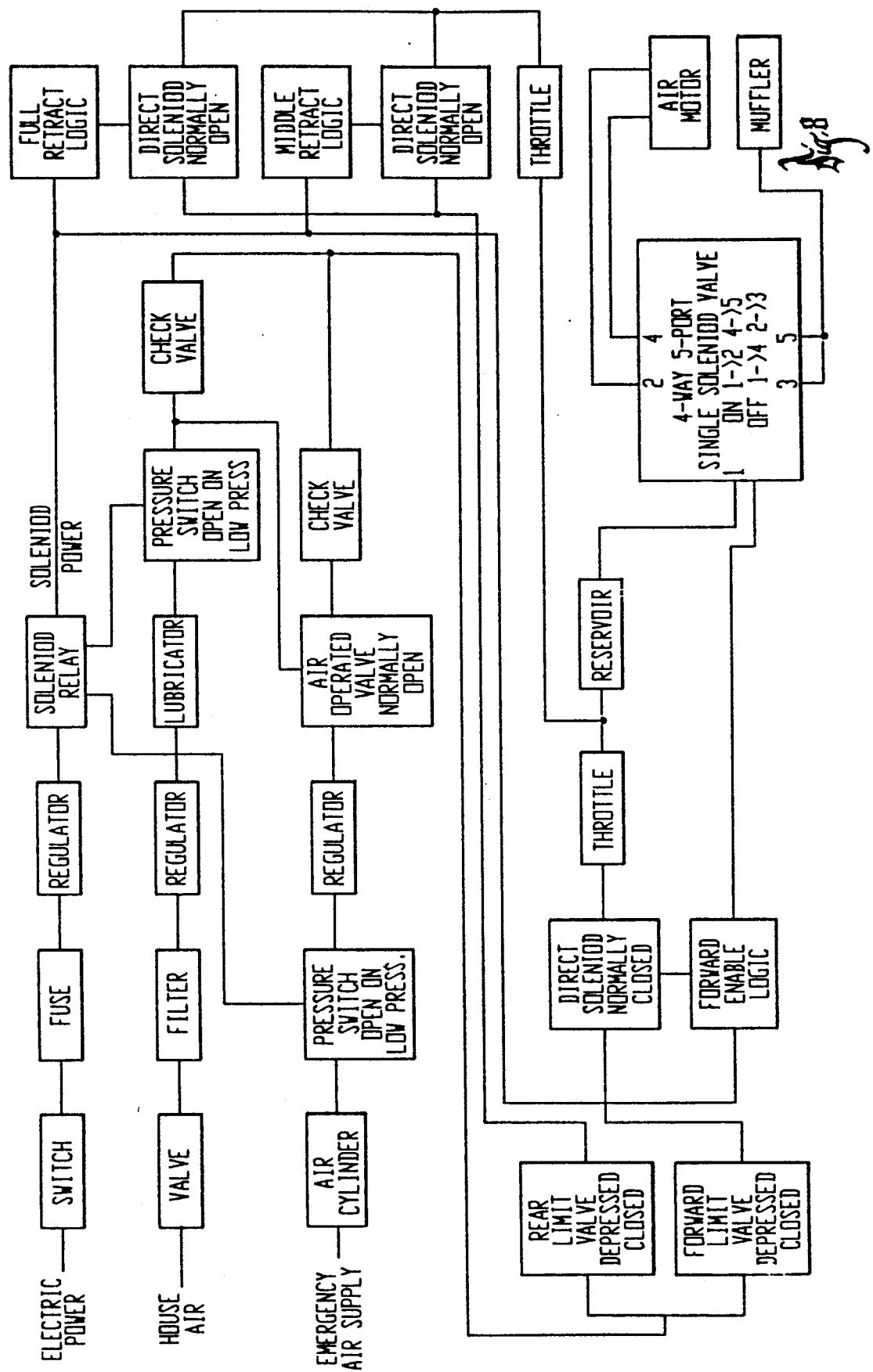
FIG. 8 is a schematic block diagram of the probe control system.

In operation, probe 10 is installed on the combustor wall 14, as shown in FIG. 1. The probe control system, shown in schematic form in FIG. 8, contains sensors and interlocks which prevent the sample coupon from being extended into the combustor unless there exists a preset minimum house air pressure sufficient for adequately cooling and maintaining the desired probe and coupon temperature, and sootblowing is not occurring within the combustion chamber in the vicinity of the sample coupon. Once the interlock conditions allow advancement of the coupon, carriage 32 is activated so as to insert the coupon into the combustion chamber. In the schematic diagram of FIG. 8, motor 22 is an airmotor, and limit valves are utilized to signal movement of the carriage or stop movement of the carriage. The limit valves also activate the house air supply to maintain the sample coupon at a set temperature as measured by the thermocouples within the carrier tube.

The probe control system is also interlocked with the combustion unit's sootblowing control system. The probe control system will receive a signal from the combustor prior to the sootblowing operation, calling for retraction of the coupon from the combustion chamber. Retraction of the coupon will close the valve 84 to seal the coupon from the combustion chamber. Upon completion of sootblowing, the coupon will automatically re-extend into the combustion chamber. This automatic operation will continue until one of the following occurs: (1) the probe is manually shut down; (2) a computer operated timer shuts down the operation of the probe; or (3) the house air/electricity/emergency compressed air supplies are below preset limits. Upon receiving one of the above signals, the coupon will retract until manually reset.

A side access panel 98 permits access to the sample coupon within the pressure shell 16 as shown in FIG. 1.

Whereas the invention has been shown and described in connection with the preferred embodiment thereof, it will be understood that many modifications, substitutions and additions may be made which are within the intended broad scope of the appended claims. There has therefore been shown and described an improved a long duration ash probe which accomplishes at least all of the above stated objectives.

We claim:

1. A probe with retractable coupon, comprising:
  a hollow, elongated pressure shell having forward and rearward ends;
  connecting means on the forward end of said shell for connecting the shell forward end to a port in a combustor such that the interior of the shell will communicate with the interior of the combustor;
  a carriage having forward and rearward ends, operably mounted within said shell for longitudinal movement between an extended position, located at the forward end of said shell, and a retracted position, located rearwardly of the forward end of the shell;
  a sample coupon removably connected to said carriage for movement therewith, and located forwardly of the carriage so as to be positioned forwardly of the connecting means when in the extended position, and located within the shell when in the retracted position;
  drive means connected to said carriage for moving said carriage forwardly and rearwardly;
  said drive means including:
  at least one guide rail from the forward to rearward end within said shell; and
  said carriage having wheel means for engaging said rail to guide the carriage therealong.

2. The probe of claim 1, wherein said drive means further comprises:
an endless loop drive cable means connected to said carriage for moving the carriage along said rail;
said drive cable means operably mounted over a forward idler sprocket and a rearward drive sprocket to form the endless loop;
said forward sprocket rotatably mounted at the forward end of the rail;
said drive sprocket rotatably mounted at the rearward end of the rail; and
a reversible motor connected to the drive sprocket to move the drive cable therealong, and thereby move the carriage.

3. The probe of claim 2, wherein said guide rail, loop drive cable, forward and rearward sprockets and carriage, are all mounted within an open frame removably inserted within said pressure shell.

4. The probe of claim 2, further comprising:
a second guide rail parallel to said at least one guide rail, within said shell;
second wheel means on said carriage for engaging said second rail;
a second endless loop drive cable means connected to said carriage;
said second drive cable means operably mounted over a forward idler sprocket at the forward end of the second rail, and a rearward drive sprocket at the rearward end of the second rail, to form the second endless loop; and
said second drive sprocket connected to said first drive sprocket for rotatable movement therewith.

5. The probe of claim 1, further comprising an operable valve means operably mounted at the forward end of said shell for selectively sealing the interior of the shell from the combustor port.

6. The probe of claim 5, further comprising control means connected to said valve means and connected to said drive means, said control means operable to operate the drive means and move said carriage to the retracted position and thence close said valve means to seal the sample coupon within said pressure shell.

7. The probe of claim 611, further comprising a heating element mounted within the said pressure shell proximal the forward end thereof, for heating the interior of the pressure shell;
said heating element connected to said control means for actuation by said control means when said coupon is retracted within said shell and said valve is closed.

8. The probe of claim 1, wherein said connecting means includes a longitudinally expandable tube connected at a rearward end to the forward end of said shell, and having means for connecting the forward end thereof to a combustor port, said expandable tube permitting thermal expansion between said shell and a combustor connected thereto.

9. The probe of claim 1, wherein said sample coupon includes a hollow tubular member having forward and rearward ends; and further comprising a hollow carrier tube having forward and rearward ends, the forward end removably connected to the rearward end of said sample coupon for fluid communication therewith, and the rearward end extending through and removably connected to said carriage for movement therewith.

10. The probe of claim 9, further comprising:
tubing within said carrier tube extending from the forward to the rearward end thereof, said tubing having an open forward end communicating with said sample coupon;
fluid conduit means connected between the rearward end of said tubing and a source of cooling fluid; and
fluid valve means interposed in said fluid conduit means and selectively operable to permit or block the flow of fluid to said tubing.

11. The probe of claim 10, further comprising sensing means mounted at the forward end of said carrier tube for sensing the temperature within the said sample coupon.

12. The probe of claim 11, further comprising control means connected to said sensing means and said fluid valve means, for operating said fluid valve means to release or block the flow of cooling fluid to said sample coupon in response to a predetermined temperature sensed by the sensing means.

13. In combination:
a combustor having an interior combustion chamber, a combustor wall, and a port in said combustor wall; and
a probe mounted to said combustor wall with a retractable coupon aligned for movement through said port;
said probe comprising:
a hollow, elongated pressure shell having forward and rearward ends;
connecting means on the forward end of said shell connecting the shell forward end to said combustor wall at said port such that the interior of the shell will communicate with the interior of the combustor;
a carriage having forward and rearward ends, operably mounted within said shell for longitudinal movement between an extended position, located at the forward end of said shell, and a retracted position, located rearwardly of the forward end of the shell;
a sample coupon removably connected to said carriage for movement therewith, and located forwardly of the carriage so as to be positioned within the combustor combustion chamber when in the extended position, and located within the shell when in the retracted position;
drive means connected to said carriage for moving said carriage forwardly and rearwardly;
said drive means including:
at least one guide rail extending from the forward to rearward end within said shell;
said carriage having wheel means for engaging said rail to guide the carriage therealong;
an endless loop drive cable means connected to said carriage for moving the carriage along said rail;
said drive cable means operably mounted over a forward idler sprocket and a rearward drive sprocket to form the endless loop;
said forward sprocket rotatably mounted at the forward end of the rail;
said drive sprocket rotatably mounted at the rearward end of the rail; and
a reversible motor connected to the drive sprocket to move the drive cable therealong, and thereby move the carriage;
an operable valve means operably mounted at the forward end of said shell for selectively sealing the interior of the shell from the combustor port;

said sample coupon including a hollow tubular member having forward and rearward ends;

a hollow carrier tube having forward and rearward ends, the forward end removably connected to the rearward end of said sample coupon for fluid communication therewith, and the rearward end extending through and removably connected to said carriage for movement therewith;

tubing within said carrier tube extending from the forward to the rearward end thereof, said tubing having an open forward end communicating with said sample coupon;

fluid conduit means connected between the rearward end of said tubing and a source of cooling fluid;

fluid valve means interposed in said fluid conduit means and selectively operable to permit or block the flow of fluid to said tubing;

sensing means mounted at the forward end of said carrier tube for sensing the temperature within the said sample coupon; and control means connected to said sensing means and said fluid valve means, for operating said fluid valve to release or block the flow of cooling fluid to said sample coupon in response to a predetermined temperature sensed by the sensing means;

said control means further connected to said valve means, said drive means, and a combustor control means, said control means operable to operate the drive means and move said carriage to the retracted position and thence close said valve means to seal the sample coupon within said pressure shell, upon receiving a signal from the combustor control means.

14. A probe with retractable coupon, comprising:

a hollow, elongated pressure shell having forward and rearward ends;

connecting means on the forward end of said shell for connecting the shell forward end to a port in a combustor such that the interior of the shell will communicate with the interior of the combustor;

a carriage having forward and rearward ends, operably mounted within said shell for longitudinal movement between an extended position, located at the forward end of said shell, and a retracted position, located rearwardly of the forward end of the shell;

a sample coupon removably connected to said carriage for movement therewith, and located forwardly of the carriage so as to be positioned forwardly of the connecting means when in the extended position, and located within the shell when in the retracted position;

drive means connected to said carriage for moving said carriage forwardly and rearwardly;

an operative valve means operably mounted at the forward end of said shell for selectively sealing the interior of the shell from the combustor port;

control means connected to said valve means and connected to said drive means, said control means operable to operate the drive means and move said carriage to the retracted position and thence close said valve means to seal the sample coupon within said pressure shell; and a heating element mounted within the said pressure shell proximal the forward end thereof, for heating the interior of the pressure shell;

said heating element connected to said control means for actuation by said control means when said coupon is retracted within said shell and said valve is closed.

* * * * *